United States Patent
Cronin

(10) Patent No.: US 11,363,970 B2
(45) Date of Patent: Jun. 21, 2022

(54) HAND-HELD DEXTERITY TESTING APPARATUS

(71) Applicant: Hunter Cronin, Bay Shore, NY (US)

(72) Inventor: Hunter Cronin, Bay Shore, NY (US)

(*) Notice: Subject to any disclaimer, the term of this patent is extended or adjusted under 35 U.S.C. 154(b) by 123 days.

(21) Appl. No.: 15/728,928

(22) Filed: Oct. 10, 2017

(65) Prior Publication Data

US 2019/0104970 A1    Apr. 11, 2019

(51) Int. Cl.
*A61B 5/11*    (2006.01)
*A61B 5/00*    (2006.01)

(52) U.S. Cl.
CPC .......... *A61B 5/1125* (2013.01); *A61B 5/0004* (2013.01); *A61B 5/4088* (2013.01); *A61B 5/4842* (2013.01); *A61B 5/7282* (2013.01); *A61B 5/742* (2013.01); *A61B 2560/0214* (2013.01); *A61B 2560/0475* (2013.01); *A61B 2562/0219* (2013.01)

(58) Field of Classification Search
None
See application file for complete search history.

(56) References Cited

U.S. PATENT DOCUMENTS

| | | | | |
|---|---|---|---|---|
| 3,265,389 A | * | 8/1966 | Carlson | A63B 23/16 482/49 |
| 5,181,181 A | | 1/1993 | Glynn | |
| 5,265,619 A | * | 11/1993 | Comby | A61B 5/1101 600/595 |
| 5,912,864 A | * | 6/1999 | Maurer | A63B 24/0021 368/10 |
| 6,151,563 A | * | 11/2000 | Marinelli | A63B 43/00 473/569 |
| 8,556,831 B1 | | 10/2013 | Faber et al. | |
| 2003/0087728 A1 | * | 5/2003 | Chen | A63B 21/028 482/44 |
| 2003/0119613 A1 | * | 6/2003 | Samuel | A63B 43/00 473/588 |
| 2008/0027671 A1 | | 1/2008 | Sano et al. | |
| 2009/0240461 A1 | | 9/2009 | Makino et al. | |
| 2011/0066397 A1 | | 3/2011 | Kranz | |
| 2011/0144539 A1 | | 6/2011 | Ouchi | |
| 2011/0181420 A1 | | 7/2011 | Mack et al. | |
| 2011/0205167 A1 | | 8/2011 | Massengill | |

(Continued)

OTHER PUBLICATIONS

"How to Spin a Basketball on Your Finger" WikiHow. Nov. 1, 2015. Retrieved Jul. 2, 2019 from <www.wikihow.com/Spin-a-Basketball-on-Your-Finger>. (Year: 2015).*

(Continued)

*Primary Examiner* — Matthew Kremer
*Assistant Examiner* — Samuel C Kim
(74) *Attorney, Agent, or Firm* — Weber Rosselli & Cannon LLP

(57) ABSTRACT

A dexterity testing apparatus includes a housing and a sensor. The housing is configured to be manipulated with digits of one hand of a user. The sensor is supported by the housing and configured to generate user dexterity data based upon changes in acceleration and orientation of the housing as the housing moves relative to the digits of the one hand of the user. The sensor is configured to convert the user dexterity data into an output signal indicative of the user's dexterity.

22 Claims, 6 Drawing Sheets

(56) References Cited

U.S. PATENT DOCUMENTS

| | | | |
|---|---|---|---|
| 2012/0080840 A1* | 4/2012 | LaRue | A63F 13/005 |
| | | | 273/138.1 |
| 2012/0124720 A1 | 5/2012 | Evans et al. | |
| 2012/0143526 A1 | 6/2012 | Benzel et al. | |
| 2012/0323520 A1 | 12/2012 | Keal | |
| 2012/0323522 A1 | 12/2012 | Turunen | |
| 2013/0035613 A1 | 2/2013 | Curtiss | |
| 2013/0046505 A1 | 2/2013 | Brunner et al. | |
| 2013/0060168 A1 | 3/2013 | Chu et al. | |
| 2013/0060515 A1 | 3/2013 | Wei et al. | |
| 2013/0073248 A1* | 3/2013 | Perkins | A63B 60/46 |
| | | | 702/141 |
| 2013/0226505 A1 | 8/2013 | Kelly et al. | |
| 2014/0024971 A1 | 1/2014 | Bunn et al. | |
| 2014/0039354 A1 | 2/2014 | Greenwald et al. | |
| 2014/0100486 A1 | 4/2014 | Alberts | |
| 2014/0163426 A1 | 6/2014 | Alberts et al. | |
| 2014/0277629 A1* | 9/2014 | Zwaschka | H01P 11/00 |
| | | | 700/91 |
| 2015/0051514 A1 | 2/2015 | Stein et al. | |
| 2015/0080766 A1 | 3/2015 | Ji et al. | |
| 2015/0126899 A1* | 5/2015 | Ghajar | G09B 5/02 |
| | | | 600/558 |
| 2015/0153381 A1 | 6/2015 | Pollatsek | |
| 2015/0173669 A1 | 6/2015 | Simon | |
| 2015/0198625 A1 | 7/2015 | Ghose et al. | |
| 2015/0220693 A1* | 8/2015 | Cadavid | A61B 5/4082 |
| | | | 424/133.1 |
| 2015/0238142 A1 | 8/2015 | Djordjevski | |
| 2015/0238143 A1 | 8/2015 | Meurer | |
| 2015/0272504 A1 | 10/2015 | Giancardo et al. | |
| 2015/0316576 A1 | 11/2015 | Pakzad et al. | |
| 2016/0058357 A1 | 3/2016 | Goble | |
| 2016/0081594 A1 | 3/2016 | Gaddipati et al. | |
| 2017/0000403 A1 | 1/2017 | Andrews | |

OTHER PUBLICATIONS

Vanbellingen, T., Kersten, B., Bellion, M., Temperli, P., Baronti, F., Muri, R., & Bohlhalter, S. (2011). Impaired finger dexterity in Parkinson's disease is associated with praxis function. Brain and Cognition, 77(1), 48-52. doi: 10.1016/j.bandc.2011.06.003 (Year: 2011).*

"plane." Merriam-Webster.com. 2020. Retrieved Oct. 7, 2020, from www.merriam-webster.com. (Year: 2020).*

The Hippest Hockey Puck Ever—The Aalto Puck. (Apr. 4, 2014). Retrieved Oct. 7, 2020, from web.archive.org/web/20140408114200/http://www.ifitshipitshere.com/hippest-hockey-puck-ever-aalto-puck/ (Year: 2014).*

Hill, B. D., Barkemeyer, C. A., Jones, G. N., Santa Maria, M. P., & Browndyke, J. N., Validation of the Coin Rotation Task: A Simple, Inexpensive, and Convenient Screening Tool for Impaired Psychomotor Processing Speed. The Neurologist, 16(4), Jul. 2010, pp. 249-253. doi:10.1097/nrl.0b013e3181b1d5b0 (Year: 2010).*

Mendoza et al., "Coin rotation task (CRT): a new test of motor dexterity", Arch Clin Neuropsychol, May 2009; 24 (3): pp. 287-292.

* cited by examiner

HAND-HELD DEXTERITY TESTING APPARATUS

TECHNICAL FIELD

The present disclosure relates to dexterity, and more particularly, to devices, systems and methods for testing dexterity to assess cognitive function.

BACKGROUND

Manual dexterity is the ability to make coordinated movements as a function of fine motor skills. Reduced dexterity in one's hand or fingers can inhibit a person's ability to grasp or manipulate objects, which can be indicative of cognitive function deficiencies. Such cognitive function deficiencies can be caused by a number of factors including sclerosis, brain injury, and/or spinal cord injury. Although various tests are available for assessing dexterity and/or cognitive function (e.g., the Knox Cube, Jebsen Hand Function Test, 9-Hole Peg Test), these tests can be expensive, time consuming, and/or inconvenient to administer. One test, the coin rotation task (CRT), is convenient to administer, but the scope of the test is effectively limited to the number of coin flips in a given time period without accounting for other nuance movement of the coin as it is flipped between the fingers of a user's hand, delimiting its accuracy.

SUMMARY

Accordingly, there is a need to provide a method, system, and/or apparatus that can track broad and nuance movements of an object that is manipulated by a user's hand to quickly and accurately test a user's dexterity. In particular, data of such movements of the object may be tracked, stored, and/or analyzed (e.g., compared to other data). For instance, data can be established from the object's movement over time to more accurately make a determination about dexterity and/or cognitive function. Such movement over time can include speed, acceleration, orientation, number of revolutions, etc., or combinations thereof. In particular, while also tracking the number of flipping revolutions, the presently disclosed dexterity testing apparatus, systems, and/or methods can perceive certain changes in speed, acceleration, and/or orientation of the presently disclosed dexterity apparatus that may be caused by a shaking or jerking of the user's hand that occurs while flipping the presently disclosed dexterity testing apparatus.

According to one aspect of the present disclosure, a dexterity testing apparatus includes a housing and a sensor. The housing is configured to be manipulated with digits of one hand of a user. The sensor is supported by the housing and configured to generate user dexterity data based upon changes in at least one of speed, acceleration, or orientation of the housing as the housing moves relative to the user. The sensor is configured to convert the user dexterity data into an output signal indicative of the user's dexterity.

In some embodiments, the sensor may include one or both of an accelerometer and a gyroscope.

In embodiments, the dexterity testing apparatus may further include a memory coupled to the sensor and configured to store one or more users' dexterity data.

In certain embodiments, the dexterity testing apparatus may further include a power source disposed in electrical communication with the sensor. The power source may be a battery.

In embodiments, the housing may define a sensor cavity that receives the sensor therein.

In some embodiments, the dexterity testing apparatus may further include a cover that mounts to the housing.

In certain embodiments, the housing may include indicia configured to count a number of revolutions of the housing as the housing is rotated relative to the one hand of the user.

In embodiments, the housing may include a first face, a second face, and an edge that extends between the first and second faces. The edge may define a non-circular outer periphery of the housing. The non-circular outer periphery of the housing may have a prolate spheroid profile.

In some embodiments, the dexterity testing apparatus may further include a display that is operatively coupled to the sensor.

In embodiments, the dexterity testing apparatus may be configured to be rotated in an end-over-end manner by the digits of the one hand of the user. The digits may consist of one or more of the user's thumb, middle finger, or index finger of the one hand of the user.

According to another aspect of the present disclosure, a dexterity testing system may be provided. The dexterity testing system may include the dexterity testing apparatus and a remote computer. The remote computer may be in communication with the sensor and configured to receive the output signal.

According to yet another aspect of the present disclosure, a method for testing dexterity with the dexterity testing apparatus may be provided. The method may include generating initial dexterity data with the sensor of the dexterity testing apparatus in response to rotation of the dexterity testing apparatus for an iteration of a predefined period.

The method may further include generating additional dexterity data with the sensor in response to additional rotation of the dexterity testing apparatus for another iteration of the predefined period, and comparing the additional dexterity data to the initial dexterity data. The method may involve enabling the sensor to selectively output a signal indicative of the user's cognition based upon the comparison of the initial and additional dexterity data.

In one aspect of the present disclosure, generating additional dexterity data with the sensor and comparing the additional dexterity data to the initial dexterity data may be performed after the user is subject to an event capable of possibly causing cognitive impairment to the user.

In yet another aspect of the present disclosure, generating initial dexterity data with the sensor may be effectuated as the dexterity testing apparatus is rotated in an end-over-end manner.

According to still another aspect of the present disclosure, a method for testing dexterity is provided. The method involves sensing movement of a dexterity testing apparatus with a sensor thereof as the dexterity testing apparatus is flipped for a predefined period between at least one of a user's thumb, middle finger, or index finger of one hand of the user. The method further includes generating dexterity data with the sensor based on one or more of: acceleration of the dexterity apparatus as the dexterity apparatus is rotated for the predefined period; speed of the dexterity apparatus as the dexterity apparatus is rotated for the predefined period; orientation of the dexterity apparatus relative to the one hand of the user as the dexterity apparatus is rotated for the predefined period; a number of revolutions of the dexterity apparatus as the dexterity apparatus is rotated for the predefined period; or a duration of one or more revolutions of the dexterity apparatus as the dexterity apparatus is rotated for the predefined period. The method further includes outputting one or more signals based on the generated dexterity data.

The method may further include comparing the generated dexterity data to different dexterity data to determine if the user is subject to possible cognitive impairment.

The method may involve storing the generated dexterity data to a memory.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the presently disclosed dexterity testing apparatus and, together with a general description of the disclosure given above, and the detailed description of the embodiment(s) given below, serve to explain the principles of the disclosure.

DETAILED DESCRIPTION

Figure 1A:
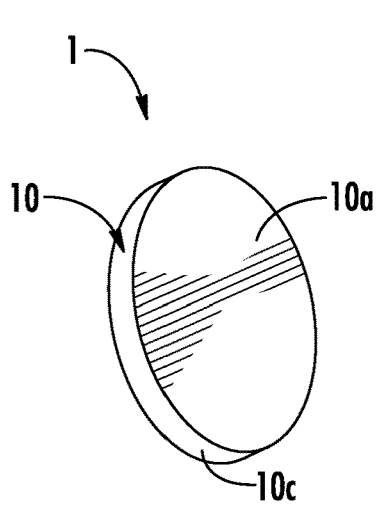
FIG. 1A is a front, perspective view of one embodiment of a dexterity testing apparatus in accordance with the principles of the present disclosure.
Figure 1B:
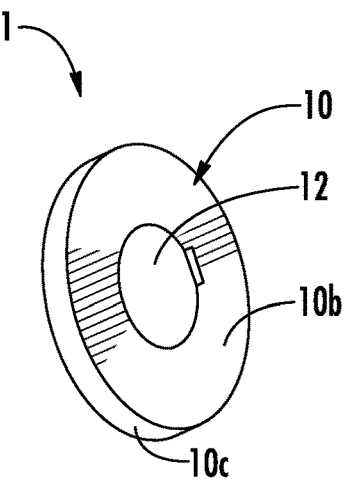
FIG. 1B is a rear, perspective view of the dexterity testing apparatus of FIG. 1A.
Figure 1C:
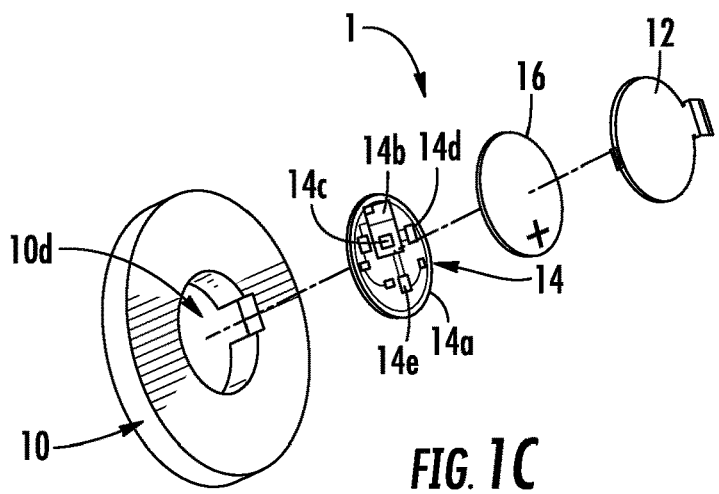
FIG. 1C is a rear, perspective view, with parts separated, of the dexterity testing apparatus of FIG. 1A.

Embodiments of the present disclosure are described in detail with reference to the drawings, in which like reference numerals designate identical or corresponding elements in each of the several views. Further, terms used herein such as "top," "bottom," "side" and similar directional terms are used simply for convenience of description and are not intended to limit the disclosure.

In the following description, well-known functions or constructions are not described in detail to avoid obscuring the present disclosure in unnecessary detail.

Referring now to FIGS. 1A-1C and 2, one embodiment of a dexterity testing apparatus of the present disclosure is generally referred to as dexterity testing apparatus 1. Dexterity testing apparatus 1 is configured to be held and manipulated by digits "D" of a user's hand "H," and, in particular, a thumb "T," middle finger "M," and index finger "I" of user's hand Dexterity testing apparatus 1 includes a housing 10 having a front face 10a, a rear face 10b, and an edge 10c that extends between the front and rear faces 10a, 10b. Housing 10 defines a cavity 10d therein that is covered by a cover 12 to support a sensor 14 and an energy source such as a battery 16 (e.g., a coin battery) in cavity 10d.

Although housing 10 of dexterity testing apparatus 1 is shown as having an oblong shape, housing 10 may have any suitable circular or non-circular shape including elliptical, oval, rectangular, diamond, etc., or combinations thereof. Such shapes may include one or more concavities and/or convexities. Such shapes may be flat, bulbous, spheroidal, smooth, rough, etc., or combinations thereof. In one embodiment, housing 10 may have a prolate spheroid shape. In some embodiments, housing 10 may include surface texturing or coatings to facilitate gripping and may include ridges, knurls, channels, bumps, apertures, etc., or combinations thereof.

Cover 12 of dexterity testing apparatus 1 is removably attachable to housing 10 of dexterity testing apparatus 1 to enable selective access to cavity 10d of housing 10, for example, to replace battery 16. Cover 12 can be secured to housing 10 using any suitable securement technique such as snap-fit, fastening, welding, etc., or combinations thereof. In some embodiments, cover 12 may be fixedly secured to housing 10 to permanently enclose battery 16 and/or sensor 14 within housing 10. In certain embodiments, one or both of battery 16 and sensor 14 may be hermetically sealed within housing 10.

Sensor 14 of dexterity testing apparatus 1 may include one or more electrical components 14a (e.g., circuit boards, circuitry, processors, central processing units, resistors, capacitors, etc., or combinations thereof). Sensor 14 includes one or more accelerometers 14b and one or more gyroscopes 14c that are electrically coupled via electrical components 14a to track movement data of dexterity testing apparatus 1 in response to a user's manipulation of dexterity testing apparatus 1 (e.g., end-over-end flipping thereof, which may be horizontal, vertical, or angular flipping) over a predefined period (e.g., 30 seconds, 1 minute, etc.) to determine user dexterity and/or cognition. Such movement data may include axial, multiaxial, planar, and/or multiplanar movement (e.g., with respect to a standard XYZ coordinate system) including, for instance, acceleration, jerk, speed, rotation, orientation, revolution duration, etc., or combinations thereof). Sensor 14 may include memory 14d coupled thereto to record or maintain such data or other relevant date (e.g., user data such as age, height, weight, prior testing results, anatomical data, etc.). In some embodiments, sensor 14 may be configured to recognize sound prompts (e.g., voice), scanned images (e.g., finger prints, retinal scans, barcodes, Aztec codes, etc.), tactile inputs (shakes, squeezes, etc.) or combinations thereof. Sensor 14 may include one or more wired or wireless communicators 14e to communicate, via signals "S" (e.g., Bluetooth, microwave radio, infrared, GPS, Wi-Fi, etc.), with a computer 18 (processor, program, controller, chip, CPU, desktop, laptop, mobile device, tablet, cell phone, etc.) that may be part of electrical components 14a of dexterity testing apparatus 1 or remote from dexterity testing apparatus 1. In some embodiments, dexterity testing apparatus 1 and computer 18 are operatively coupled to form a dexterity testing system 1x.

In embodiments, computer 18 may support an app, program, platform, software, algorithm, etc. configured to communicate with dexterity testing apparatus 1 or components thereof (e.g., sensor 14). In embodiments, dexterity testing apparatus 1 (e.g., computer 18 and/or sensor 14) may be configured to sense and/or process data with respect to multiple users. For instance, each player of a team can be recorded (e.g., stored in memory via a unique profile) so that historical data of each player can be generated over time. For instance, such data can be recalled and compared against (e.g., as baseline data for comparison against current data) and/or otherwise used to assess dexterity and/or cognitive conditions over time (e.g., including currently). In particular, testing of each player with dexterity testing apparatus 1 can be performed weekly, monthly, yearly, etc. to determine dexterity changes and/or if there is a possibility of cognitive impairment. To the extent that dexterity changes are indicated by test data generated from dexterity testing apparatus 1 that indicates loss in dexterity and/or possible loss of cognitive function, a user can then seek medical assistance and/or more thorough testing (e.g., a medical examination, and/or scanning such as with Mill, CT, PET, etc.) to determine if cognitive impairment exists. Such data can also be compared between users or other data (e.g., charted data indicative of typical and/or atypical ranges, deviations, etc. of dexterity and/or cognition of the user, other users, and/or other known data).

Battery 16 of dexterity testing apparatus 1 is electrically coupled to sensor 14 to power dexterity apparatus 1. Battery 16 can be any suitable battery including replaceable, rechargeable, lithium-ion, etc. In certain embodiments, battery 16 may be charged via an electrical outlet (e.g., wired). In some embodiments, battery 16 may be operatively coupled to one or more photovoltaic elements to enable battery 16 to be charged via solar energy.

Figure 2:
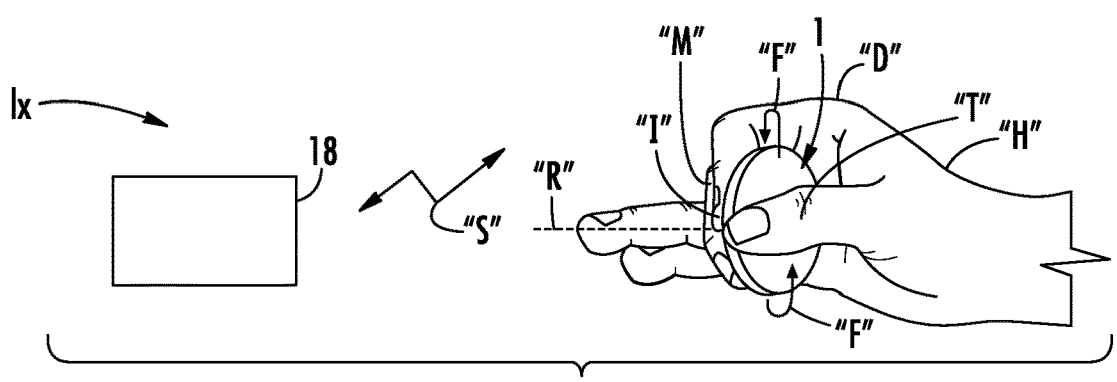
FIG. 2 is a side view illustrating the dexterity testing apparatus of FIG. 1A being flipped by digits of a user's hand while communicating with a computer.
Figure 2A:
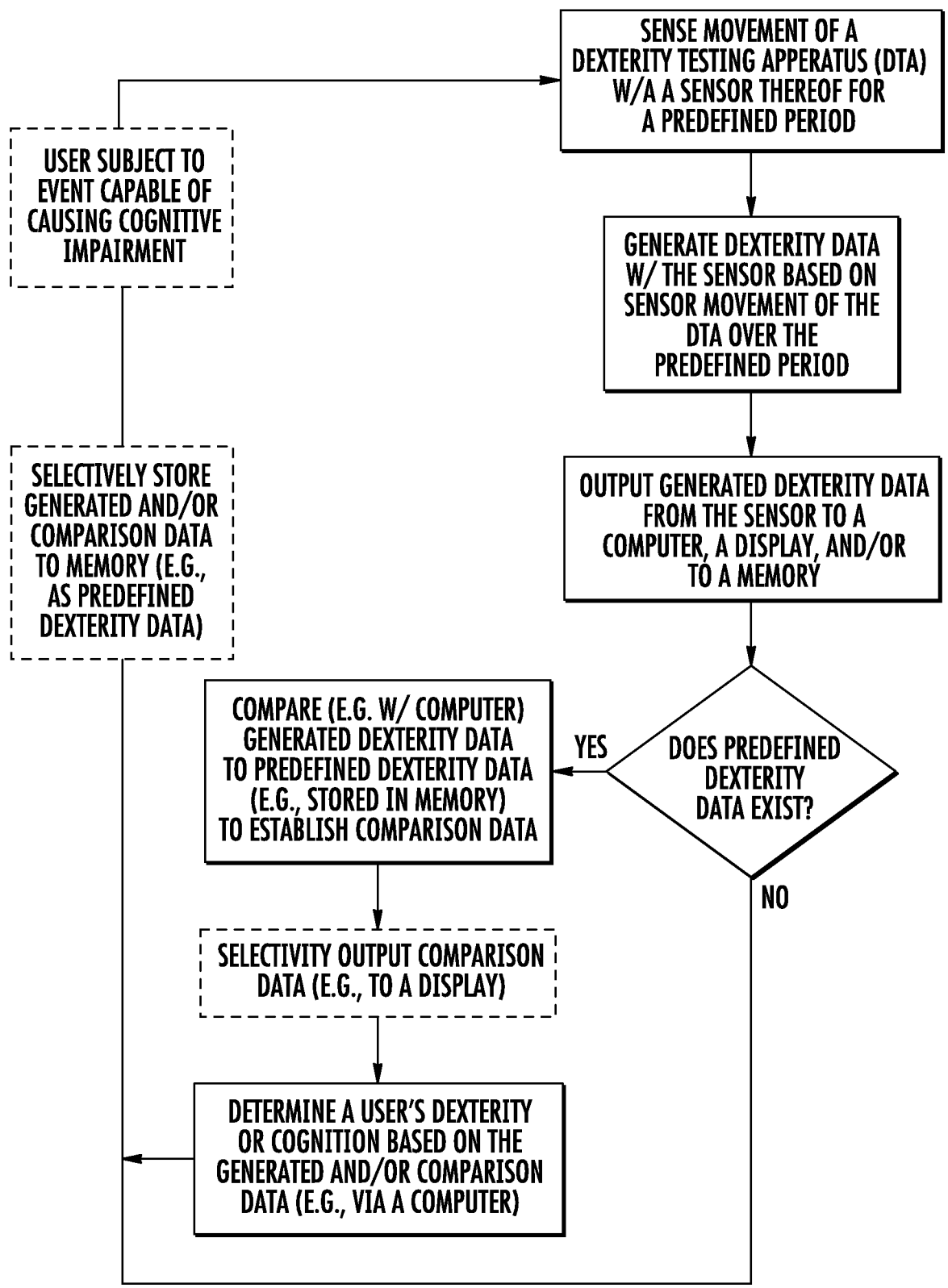
FIG. 2A is a flow chart illustrating dexterity testing with the dexterity testing apparatus of FIG. 1A.
Figure 3:
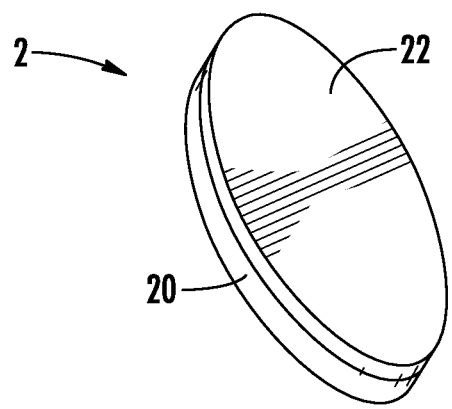
FIG. 3 is a front, perspective view of another embodiment of a dexterity testing apparatus in accordance with the principles of the present disclosure.

With reference to FIGS. 2 and 2A, in use, a user grasps dexterity testing apparatus 1 with digits "D," namely, the thumb "T," index finger "I," and middle finger "M" of one hand "H." With dexterity testing apparatus 1 in communication with computer 18 (e.g., software, program, app, etc.), the user can then initiate a dexterity test by rotating dexterity testing apparatus 1 with digits "D" of the user's hand "H" about a rotation axis "R" defined centrally through dexterity testing apparatus 1, by flipping dexterity testing apparatus 1 in an end-over-end (e.g., 180 degrees) fashion, as illustrated by arrows "F," for a predefined period. As the dexterity testing apparatus 1 is rotated, sensor 14 thereof collects or generates dexterity data based on sensed movement of dexterity testing apparatus 1 over the predefined period (e.g., 30 seconds) and outputs or communicates the generated dexterity data from sensor 14 to computer 18 (and/or to a display and/or to memory).

The generated dexterity data can then be analyzed and/or stored (via computer or manually such as being written on paper). For example, such data can be compared to other preexisting or predefined data, such as from other dexterity tests completed by the instant user or other users, and/or other informational databases related to dexterity and/or cognition. Such comparison can provide additional and/or comparison data for outputting to a display, analysis, and/or storage to memory, and which may be used to determine a user's dexterity or cognition (e.g., an impairment thereof).

Subsequent dexterity tests can be run as desired for comparison with, for instance, the initial dexterity test. For example, such subsequent dexterity tests can be run after a user is subject to an event that is capable of causing cognitive impairment (e.g., a brain or spinal injury) to make a determination about dexterity and/or cognitive impairment resulting from the event. In particular, the initial dexterity test may provide better results (e.g., more flips, less changes in acceleration, orientation, jerk, etc.; faster spins, etc.) when compared to the subsequent dexterity test and such differences, perhaps if significant (e.g., greater than 10 percent, 20 percent, etc. deviation), may indicate deficiencies in dexterity and, thus, cognitive impairment.

Figure 4:
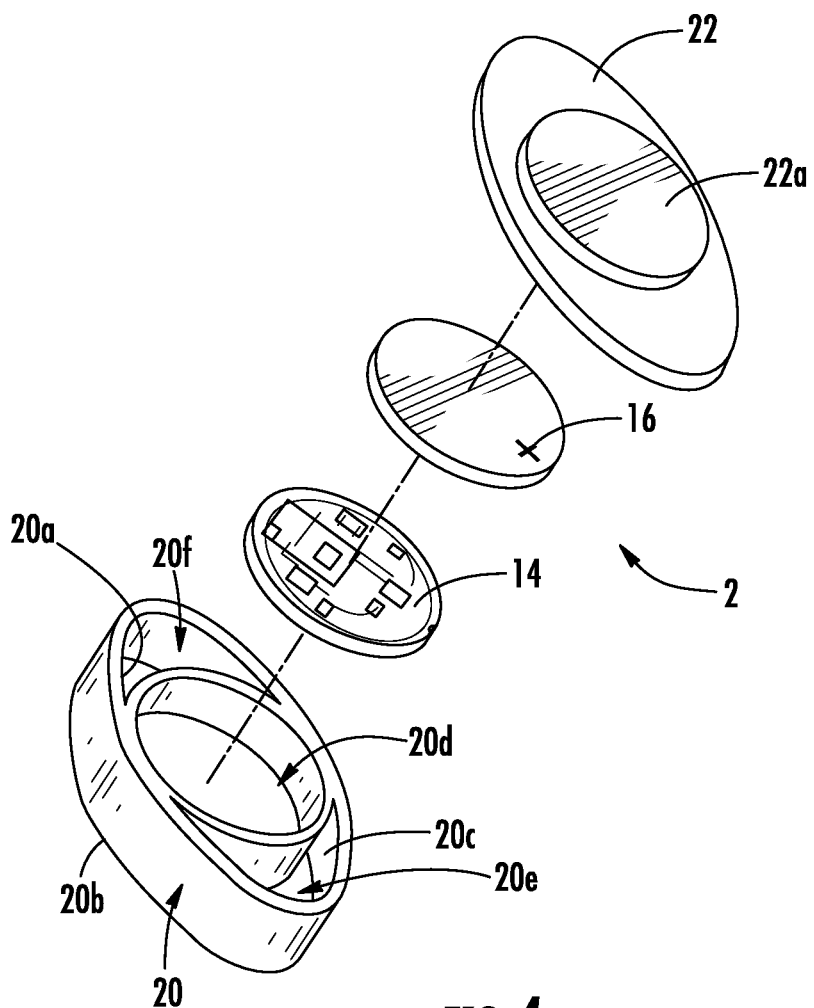
FIG. 4 is a perspective view, with parts separated, of the dexterity testing apparatus of FIG. 3.

Turning now to FIG. 4, another embodiment of a dexterity testing apparatus 2 includes having a prolate spheroid profile (e.g., football shape). Dexterity testing apparatus 2 includes housing 20 and a cover 22 that may be selectively coupled thereto for supporting sensor 14 and battery 16 therein. Housing 20 includes a base 20a that supports an oblong side edge 20b. Oblong side edge 20b surrounds a central ring 20c and extends along an outer periphery of dexterity testing apparatus 2 to define the prolate spheroid profile. Housing 20 includes a central cavity 20d defined by inner surfaces of central ring 20c and base 20a. An outer surface of central ring 20c and an inner surface of oblong side edge 20b define a pair of arched troughs 20e, 20f disposed on opposite sides of central ring 20c. The arched troughs 20e, 20f may include a parabolic profile. Cover 22 includes a protuberance 22a that is configured to frictionally engage central cavity 20d to retain cover 22 on housing 20 and maintain sensor 14 and battery 16 within central cavity 20d.

Figure 4A:
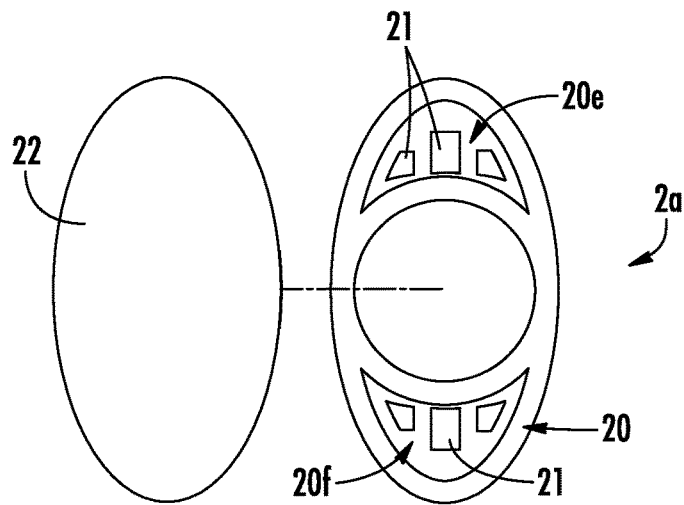
FIG. 4A is a perspective view, with parts separated, of still another embodiment of a dexterity testing apparatus in accordance with the principles of the present disclosure.

In another embodiment, as illustrated in FIG. 4A, a dexterity testing apparatus, generally referred to as dexterity testing apparatus 2a, is similar to dexterity testing apparatus 2, but includes one or more components 21 within arched troughs 20e, 20f. The one or more components may include timers, sensors, microphones, speakers, clocks, weights, batteries, electrical components, wiring, chips, alarms (e.g., audible, tactile, and/or visible devices such as LED's, horns, vibrators, etc.), or combinations thereof.

Figure 4B:
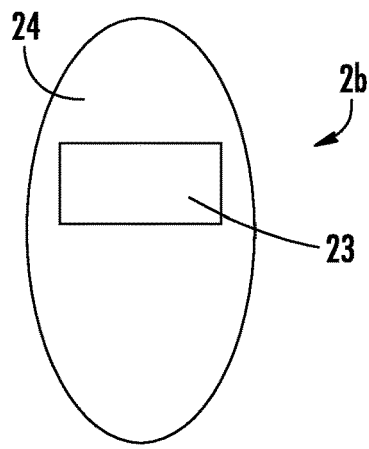
FIG. 4B is a front view of yet another embodiment of a dexterity testing apparatus in accordance with the principles of the present disclosure.

As seen in FIG. 4B, one embodiment of a dexterity testing apparatus 2b may include a display (e.g., an LED display) supported on a face 24 of dexterity testing apparatus 2b for outputting data and/or alarms, device status (e.g., on/off/start/stop, etc., or combinations thereof).

Figure 4C:
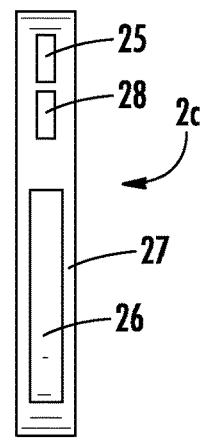
FIG. 4C is a side view of a further embodiment of a dexterity testing apparatus in accordance with the principles of the present disclosure.

With reference to FIG. 4C, one embodiment of a dexterity testing apparatus 2c may include one or more actuators 25 such as a switch, knob, slide, button, etc., or combinations thereof, to activate one or more components of dexterity testing apparatus 2c (e.g., sensor). For instance, actuator 25 may be coupled to an indicia 28 (e.g., a counter) and sensor 14 (FIG. 1C) for counting revolutions of dexterity testing apparatus 2c over a predefined period to track movement/data of dexterity testing apparatus 2c as dexterity testing apparatus 2c is manipulated by a user during a dexterity test. Dexterity testing apparatus 2c further includes a side display 26 on an edge 27 thereof that can provide information such as status of dexterity testing apparatus 2c (e.g., start/stop/on/off, etc.), warnings (e.g., malfunction, possible cognitive impairment, concussion, etc.), test number, date, time, duration, etc., or combinations thereof.

Figure 5A:
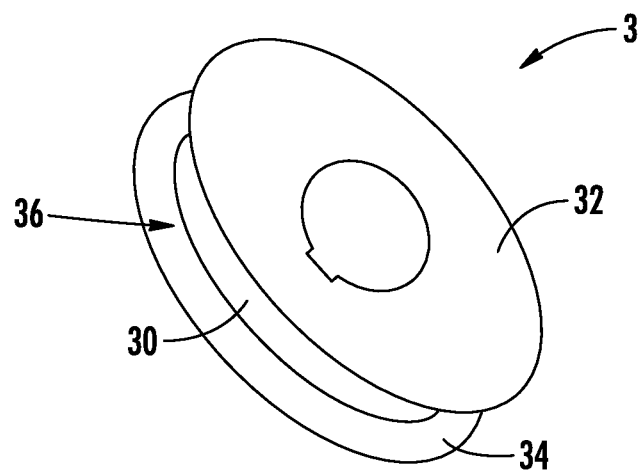
FIG. 5A is a rear, perspective view of one embodiment of a dexterity testing apparatus in accordance with the principles of the present disclosure.
Figure 5B:
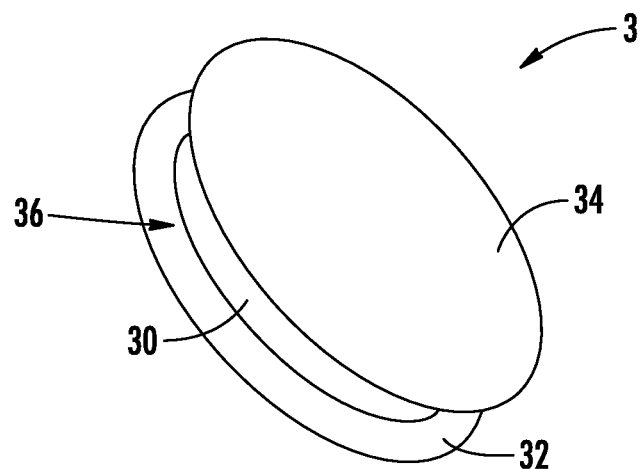
FIG. 5B is a top, perspective view of the dexterity testing apparatus of FIG. 5A.

As seen in FIGS. 5A and 5B, another embodiment of a dexterity testing apparatus is generally referred to as dexterity testing apparatus 3. Dexterity testing apparatus 3 has a central body 30 and first and second plates 32, 34 that extend outwardly from body 30 to define an outer channel 36 about body 30. First and second plates 32, 34 and channel 36 are positioned to facilitate manipulation, gripping, and/or flipping of dexterity testing apparatus 3 as dexterity testing apparatus 3 is flipped with a user's hand "H" (FIG. 2) during a dexterity test.

Figure 6A:
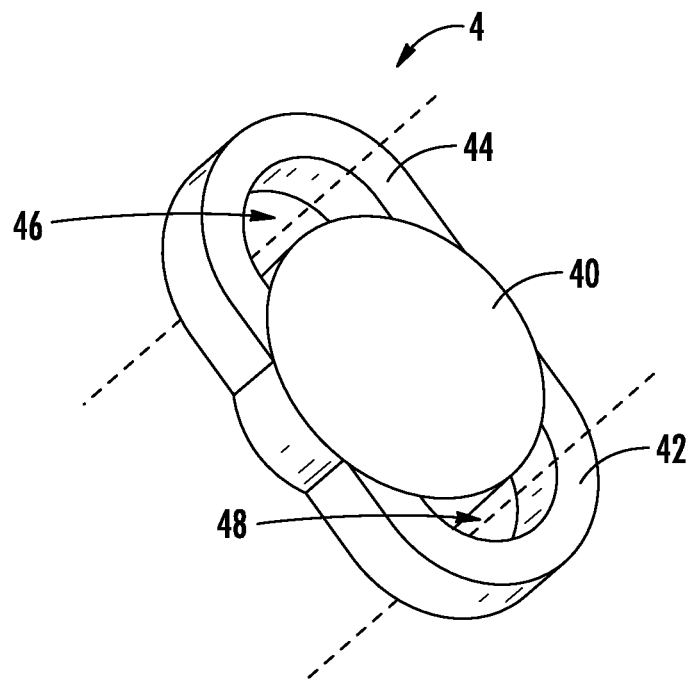
FIG. 6A is a top, perspective view of one embodiment of a dexterity testing apparatus in accordance with the principles of the present disclosure.
Figure 6B:
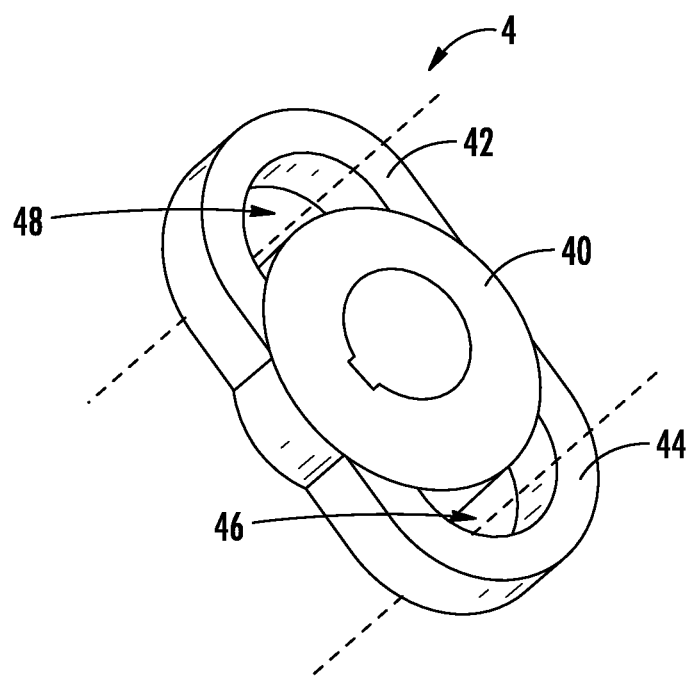
FIG. 6B is a rear, perspective view of the dexterity testing apparatus of FIG. 6A.

With reference to FIGS. 6A and 6B, still another embodiment of a dexterity testing apparatus is generally referred to as dexterity testing apparatus 4. Dexterity testing apparatus 4 has a central body 40 having first and second arched arms 42, 44 extending therefrom on opposite sides of central body 40. Throughholes 46 and 48 are defined between first and second arched arms 42, 44 and sides of central body 40, respectively. Arched arms 42, 44 and throughholes 46, 48 are also configured to facilitate manipulation, gripping, and/or flipping of dexterity testing apparatus 4 during a dexterity test.

Any of the components of the presently described devices can be formed of any suitable natural or synthetic material such as metals, polymers, ceramics, minerals, wood, glass, etc., or combinations thereof such that the presently described devices, or components thereof, may be rigid and/or flexible. Securement of any of the components of the presently described devices to any of the other components of the presently described devices can be effectuated using known securement techniques such welding (e.g., ultrasonic), crimping, gluing, fastening, interference-fit, snap-fit, etc., or combinations thereof.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

The invention claimed is:

1. A dexterity testing apparatus, comprising:
   a rigid housing configured to be rotated in an end-over-end manner between digits of one hand of a user, the housing including a first planar face, a second face, and a side edge extending between the first planar face and the second face along an outer periphery of the first planar face, the side edge defining an outer periphery of the housing, wherein the housing includes a central body having a first and second arched arms extending therefrom on opposite sides of the central body, the first arched arm spaced from the central body by a first through hole, and the second arched arm spaced from the central body by a second through hole;
   a sensor supported by the housing and configured to generate user dexterity data based upon changes in at least one of speed, acceleration or orientation of the housing as the housing moves relative to the user, the sensor configured to convert the user dexterity data into an output signal indicative of the user's dexterity.

2. The dexterity testing apparatus of claim 1, wherein the sensor includes at least one of an accelerometer and a gyroscope.

3. The dexterity testing apparatus of claim 1, further comprising a memory coupled to the sensor and configured to store at least one user's dexterity data.

4. The dexterity testing apparatus of claim 1, further comprising a power source disposed in electrical communication with the sensor.

5. The dexterity testing apparatus of claim 4, wherein the power source is a battery.

6. The dexterity testing apparatus of claim 1, wherein the housing defines a sensor cavity that receives the sensor therein.

7. The dexterity testing apparatus of claim 1, further comprising a cover that mounts to the housing.

8. The dexterity testing apparatus of claim 1, wherein the housing includes indicia configured to count a number of revolutions of the housing as the housing is rotated relative to the one hand of the user.

9. The dexterity testing apparatus of claim 1, wherein the housing has a prolate spheroid profile.

10. The dexterity testing apparatus of claim 1, further comprising a display that is operatively coupled to the sensor.

11. A dexterity testing system including the dexterity testing apparatus of claim 1 and a remote computer, the remote computer in communication with the sensor and configured to receive the output signal.

12. A method for testing dexterity with the dexterity testing apparatus of claim 1, the method comprising:
    generating initial dexterity data with the sensor of the dexterity testing apparatus in response to rotation of the dexterity testing apparatus for an iteration of a predefined period.

13. The method of claim 12, further comprising generating additional dexterity data with the sensor in response to additional rotation of the dexterity testing apparatus for another iteration of the predefined period, and comparing the additional dexterity data to the initial dexterity data.

14. The method of claim 13, further comprising enabling the sensor to selectively output a signal indicative of the user's cognition based upon the comparison of the initial and additional dexterity data.

15. The method of claim 14, wherein generating additional dexterity data with the sensor and comparing the additional dexterity data to the initial dexterity data is performed to determine if the user is subject to cognitive impairment.

16. The method of claim 12, wherein generating initial dexterity data with the sensor is effectuated as the dexterity testing apparatus is rotated in the end-over-end manner.

17. The dexterity testing apparatus of claim 1, wherein the housing is configured to be rotated in the end-over-end manner between at least two of the user's thumb, middle finger, or index finger of the one hand of the user.

18. The dexterity testing apparatus of claim 1, wherein the side edge surrounds a central ring including an inner surface and an outer surface, the inner surface of the central ring and a portion of the first planar face define a central cavity inside the housing, the central cavity configured to receive at least the sensor therein.

19. The dexterity testing apparatus of claim 18, wherein the second face includes a protuberance configured to frictionally engage the central cavity to retain the second face to the housing.

20. A method for testing dexterity, the method comprising:
    sensing movement of a dexterity testing apparatus including a rigid housing with a sensor thereof as the dexterity testing apparatus is flipped for a predefined period between at least two or more of a user's thumb, middle finger, or index finger of one hand of the user;

generating dexterity data with the sensor based on at least one of:

acceleration of the dexterity apparatus as the dexterity apparatus is rotated for the predefined period;

speed of the dexterity apparatus as the dexterity apparatus is rotated for the predefined period;

orientation of the dexterity apparatus relative to the one hand of the user as the dexterity apparatus is rotated for the predefined period;

comparing the generated dexterity data to different dexterity data to determine if the user is subject to a concussion; and outputting at least one signal based on the generated dexterity data.

21. The method of claim 20, further comprising storing the generated dexterity data to a memory.

22. A method for testing dexterity, the method comprising:

sensing movement of a dexterity testing apparatus including a rigid housing with a sensor positioned therein as the dexterity testing apparatus is flipped for a predefined period between at least two or more of a user's thumb, middle finger, or index finger of one hand of the user;

generating dexterity data with the sensor based on at least one of:

acceleration of the dexterity apparatus as the dexterity apparatus is rotated for the predefined period;

speed of the dexterity apparatus as the dexterity apparatus is rotated for the predefined period;

orientation of the dexterity apparatus relative to the one hand of the user as the dexterity apparatus is rotated for the predefined period;

a number of revolutions of the dexterity apparatus as the dexterity apparatus is rotated for the predefined period; or a duration of at least one revolution of the dexterity apparatus as the dexterity apparatus is rotated for the predefined period; and comparing the generated dexterity data to different dexterity data to determine if the user is subject to a concussion.

* * * * *